(12) United States Patent
Zhao et al.

(10) Patent No.: US 8,894,707 B2
(45) Date of Patent: Nov. 25, 2014

(54) TENDON OR LIGAMENT TISSUE ENGINEERING

(75) Inventors: Chunfeng Zhao, Rochester, MN (US);
Yu-long Sun, Rochester, MN (US);
Steven L. Moran, Rochester, MN (US);
Kai-Nan An, Rochester, MN (US);
Peter C. Amadio, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 277 days.

(21) Appl. No.: 13/254,784

(22) PCT Filed: Mar. 2, 2010

(86) PCT No.: PCT/US2010/025870
§ 371 (c)(1),
(2), (4) Date: Sep. 2, 2011

(87) PCT Pub. No.: WO2010/101883
PCT Pub. Date: Sep. 10, 2010

(65) Prior Publication Data
US 2011/0319993 A1 Dec. 29, 2011

Related U.S. Application Data

(60) Provisional application No. 61/158,091, filed on Mar. 6, 2009.

(51) Int. Cl.
*A61F 2/08* (2006.01)
*A61L 27/36* (2006.01)
*A61L 27/48* (2006.01)

(52) U.S. Cl.
CPC ......... *A61L 27/3683* (2013.01); *A61L 2430/10* (2013.01); *A61L 27/3604* (2013.01); *A16L 27/38* (2013.01); *A61F 2/08* (2013.01); *A61L 27/48* (2013.01)
USPC ........................................ 623/13.11; 435/1.1

(58) Field of Classification Search
None
See application file for complete search history.

(56) References Cited

U.S. PATENT DOCUMENTS

| 5,514,181 | A |   | 5/1996  | Light et al. |
| 6,090,996 | A | * | 7/2000  | Li ............................... 623/23.64 |
| 2002/0128724 | A1 |   | 9/2002  | Ollerenshaw et al. |
| 2004/0076657 | A1 |   | 4/2004  | Wolfinbarger et al. |
| 2005/0013870 | A1 | * | 1/2005  | Freyman et al. ............. 424/520 |
| 2007/0185585 | A1 | * | 8/2007  | Bracy et al. ................. 623/23.63 |
| 2007/0248638 | A1 | * | 10/2007 | Van Dyke et al. ............ 424/422 |

OTHER PUBLICATIONS

Zimny et al., The Anatomical Record, vol. 214: 204-209 (1986).*
Omae et al., "Multilayer Tendon Slices Seeded with Bone Marrow Stromal Cells: A Novel Composite for Tendon Engineering," *J. Orthoped. Res.*, 2009, 27(7):6 pages.
International Search Report and Written Opinion in International Application No. PCT/US2010/025870, mailed Nov. 18, 2010, 13 pages.
International Preliminary Report on Patentability in International Application No. PCT/US2010/025870, issued Sep. 6, 2011, 8 pages.

* cited by examiner

*Primary Examiner* — Allison Fox
*Assistant Examiner* — Yvonne Pyla
(74) *Attorney, Agent, or Firm* — Fish & Richardson P.C.

(57) ABSTRACT

This document relates to methods and materials involved in tendon or ligament tissue engineering. For example, methods and materials for generating a composite of acellular tendon or ligament allograft slices seeded with cells and bundled into a graft for tissue repair are provided.

12 Claims, 11 Drawing Sheets

TENDON OR LIGAMENT TISSUE ENGINEERING

CROSS-REFERENCE TO RELATED APPLICATIONS

This application is a National Stage application under 35 U.S.C. 371 and claims benefit under 35 U.S.C. 119(a) of International Application No. PCT/US2010/025870, having an International Filing Date of Mar. 2, 2010, which claims the benefit of priority to U.S. Provisional Application Ser. No. 61/158,091, filed on Mar. 6, 2009. The disclosures of the prior applications are considered part of (and are incorporated by reference in) the disclosure of this application.

BACKGROUND

1. Technical Field

This document relates to methods and materials involved in tendon or ligament tissue engineering. For example, this document provides methods and materials for generating a composite of acellular tendon or ligament allograft slices seeded with cells and bundled into a graft for tissue repair.

2. Background Information

Tendon injuries are very common and place a large burden on the US economy. It has been estimated that more than 32 million patients sustain traumatic and overuse injuries to tendons and ligaments, at a cost of roughly $30 billion per year. Functional restoration of the injured tendon is still a great challenge. Similarly, ligaments, which are poorly vascularized, do not heal well and usually must be replaced after significant damage has occurred.

SUMMARY

This document provides methods and materials related to tendon or ligament tissue engineering. For example, this document provides methods and materials related to engineering tendon or ligament tissue for human, equine, or other mammalian clinical uses. As described herein, allogenic decellularized fresh tissue is in many ways an ideal scaffold environment for cell seeding, adhesion, and survival, containing native collagen, with normal tissue structure and organization. As described herein, this document provides methods and materials for generating composite tissue engineered tendons and composite tissue engineered ligaments from tendon and ligament allograft slices, respectively. In some cases, the composite of acelluar tissue slices can be seeded with autologous stem cells and/or bundled into a thicker composite for surgical grafting or implantation. This document also provides methods and materials for using a composite tissue engineered tendon or ligament for regenerating, repairing, or replacing damaged tendon or ligament. As described herein, this document provides, for example, methods and materials by which a multilayer composite of tendon or ligament allograft slices can be fabricated to serve as a scaffold for tendon or ligament regeneration that possesses the basic structure of the tendon or ligament, a native extracellular matrix, and the capability of cell seeding and cellular ingrowth. The methods and materials provided herein can allow fabrication of a wide array of tendon and ligament substitutes, varying in size and strength.

In general, one aspect of this document features a composition comprising, or consisting essentially of, multiple layers of tendon or ligament portions. The tendon or ligament portion can be obtained from a mammal and decellularized to remove a mammal's cells from the portion. The composition can comprise tendon portions. The composition can comprise ligament portions. The composition can have portions that are decellularized to lack a mammal's cells. The composition can further comprise one or more layers. The composition can further comprise an extracellular matrix of tendon or ligament portions. The mammal can be a human. The composition can be seeded with a plurality of cells. The cells can be autologous stem cells. The autologous stem cells can be derived from bone marrow, tendon, ligament, muscle, adipose, or synovial tissue. The composition can be coated with a lubricating surface. The composition can further comprise one or more growth factors. The growth factors can be GDF5, TGF-β, VEGF, PDGF, BMPs, or any combination thereof. The composition can be reinforced by adding one or more layers of man-made material.

In another aspect, this document features a method for providing a tendon or ligament tissue implant to a mammal. The method comprises, or consists essentially of, implanting a composition into said mammal. The composition can comprise multiple layers of tendon or ligament portions. The portions can be from a mammal and decellularized to remove a mammal's cells from a portion. The method can further comprise providing an implant for repairing tendon or ligament tissue damage. The method can further comprise providing an implant for replacing damaged tendon or ligament tissue of a mammal with an implant. The multiple layers of tendon or ligament portions of a composition can be sutured to form a roll. The roll can be implanted into tendon or ligament tissue of a mammal.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document relates to methods and materials involved in tendon or ligament tissue engineering. As described herein, this document also provides methods and materials for generating composite tissue engineered tendons and composite tissue engineered ligaments from tendon and ligament allograft slices, respectively.

This document provides methods and materials for a composition of multiple layers of tendon or ligament tissue portions. Any appropriate human cadaver tendon or ligament tissue portions can be used. Tendon or ligament portions can be harvested from any suitable body parts. For example, tendon or ligament portions can be harvested from the leg, arm, back, hand, or foot. In some cases, tendons harvested for the methods and materials described herein can be, for example, the Achilles tendon, infraspinatus tendon, tibialis anterior tendon, peroneus longus tendon, peroneus medius tendon, extensor digitorum longus tendons, extensor hallucis longus tendon, flexor digitorum longus tendon, or patellar tendon. In some cases, ligaments harvested for the methods and materials described herein can be, for example, the ulnar collateral ligament, radial collateral ligament, medical collateral ligament, lateral collateral ligament, anterior cruciate ligament, posterior cruciate ligament, anterior or posterior talofibular ligaments, calcaneofibular ligament, talocalcaneal ligament, or posterior talocalcaneal ligament. Harvested tendon and ligament portions can be of any suitable size and shape. For example, tendon and ligament tissue portions can be rectangular, square, circular, oval, or other shapes, or include the entire tendon or ligament, as needed. Tendon and ligament tissue harvested for use in the methods and materials provided herein can be used as freshly harvested tissue, or can be stored (e.g., frozen at −80° C., freeze-dried).

Tendon and ligament tissue harvested for use in the methods and materials provided herein can be decellularized to remove the native cells. Any appropriate method can be used to remove native cells from tendon and ligament tissue while maintaining morphological integrity of the tissue portions and preserving extracellular matrix (ECM) proteins. For example, decellularization methods can include subjecting tendon and ligament tissue to repeated freeze-thaw cycles using liquid nitrogen. The tissue can also be treated with a nuclease solution (e.g., ribonuclease, deoxyribonuclease) and washed in sterile phosphate buffered saline with mild agitation. Mild, non-ionic detergents such as TRITON® X-100 (Union Carbide Corp.) or anionic detergents such as sodium deoxycholate, or sodium dodecylsulfate can be used to aid decellularization. The extent of decellularization can be assayed by hematoxylin and eosin staining or Movat-Pentachrome staining Electron microscopy can be used to assay for morphological integrity of the decellularized tissue portions. Conservation of extracellular matrix (ECM) proteins can be assayed by immunohistochemical staining against laminin and collagens I and IV.

This document also provides methods and materials for combining tendon and ligament portions with other portions to form a composite of any size or shape. For example, a tendon tissue portion can be combined with additional tendon tissue portions to form a multilayered composite of tendon tissue portions. Similarly, a ligament tissue portion can be combined with other ligament tissue portions to form a multilayered composite of ligament tissue portions. Tendon or ligament portions can be combined by stacking multiple tissue layers to form a composite. In some cases, tendon or ligament portions can be rolled together using different weaving techniques to form a tissue composite. In some cases, tendon or ligament portions can be combined by weaving tissue portions together to form a tissue composite. A tissue composite of tendon or ligament portions can be provided as a bundle or cut into slices of varying thicknesses. For example, a tissue composite of tendon or ligament portions can be cut length-wise to produce slices having a thickness of about 100 or more micrometers (e.g., about 100-500 μm, 100-400 μm, 100-300 μm, 100-200 μm, 200-500 μm, 300-500 μm, or 400-500 μm). In some cases, a tissue composite of tendon or ligament portions can be embedded in a compound (e.g., Tissue-Tek® optimal cutting temperature compound (Sakura Finetek USA, Inc., USA)) to facilitate cutting. For example, a microtome (e.g., cryostat) can be used to cut an embedded composite into slices with thicknesses of about 100, 200, 300, 400, or 500 μm. In some cases, tendon or ligament composites can be manually cut by into slices.

This document also provides methods and materials for seeding tendon and ligament portions with cells. Any appropriate cell type, such as naïve or undifferentiated cell types, can be used to seed the tissue portions or composite tendon and ligament tissue. For example, stem cells from any tissue source (e.g., skin, bone, synovium, adipose tissue, bone marrow, peripheral blood, umbilical cord blood, or muscle) can be used to seed tendon and ligament tissue. In some cases, autologous cells can be used to seed a tendon or ligament portion. In such cases, tendon or ligament portions and cells are obtained for transplantation into the same individual. Any appropriate method for isolating and collected cells for seeding can be used. For example, bone marrow stromal cells can be readily harvested from bone marrow. Peripheral blood stem cells can be collected from the blood through a process known as apheresis. Isolated cells can be rinsed in a buffered solution (e.g., phosphate buffered saline) and resuspended in a cell culture medium. In some cases, cells can be collected and cryopreserved for later seeding of tendon or ligament portions. For example, bone marrow and other cell types can be frozen for prolonged periods (e.g., cryopreserved).

Standard cell culture methods can be used to culture and expand the population of cells. The cells can be differentiated into tenocytes by stimulation with cytokines such as TGF-β.

Such differentiation can be monitored by the expression of tendon-specific markers such as tenomodulin, thrombospondin-4, and scleraxis. Upon differentiation, the cells can be contacted with the tendon or ligament to seed tendon and ligament tissue portions. To facilitate seeding, the portions can be cut into slices roughly 300 micrometers in thickness. Portions of such a thickness can retain the strength and architecture of the native tendon or ligament, while amplifying the surface area and minimizing the needed depth of penetration of the cells being seeded. In some cases, portions can be cut into slices having other thicknesses (e.g., about 100-500 µm, 100-400 µm, 100-300 µm, 100-200 µm, 200-500 µm, 300-500 µm, or 400-500 µm) Tissue portions or composites of tendon or ligament tissue can be seeded with cells in vitro. Various seeding densities can be used. For example, cell densities from $0.2 \times 10^6$ to $0.2 \times 10^7$ cells/composite can be used. In some cases, the seeded tissue or composite tissue can be incubated for a period of time (e.g., 1, 2, 3, 4, 5, 6, 7, 8, 10, 12, 14, or more days) post-seeding to improve fixation and penetration of the cells in the composite. For example, the seeded tissue or composite tissue can be incubated under conditions appropriate to promote cell growth and differentiation. In some cases, seeded tissue or composite tissue can be incubated at about 37° C. with 5% $CO_2$ at 100% humidity. Histology and cell staining can be performed to assay for seeded cell propagation. Any appropriate method can be performed to assay for seeded cell differentiation. For example, quantitative real-time reverse transcription-polymerase chain reaction (RT-PCR) can be performed to detect and measure expression levels of markers of tenocyte differentiation (e.g., tenomodulin, scleraxis), gelatinase (e.g., MMP2), and collagenase (e.g., MMP13). Any appropriate RT-PCR protocol can be used. Briefly, total RNA can be collected by homogenizing a biological sample (e.g., tendon sample), performing a chloroform extraction, and extracting total RNA using a spin column (e.g., RNeasy® Mini spin column (QIAGEN, Valencin, Calif.)) or other nucleic acid-binding substrate. In some cases, in situ hybridization can be performed on tendon or ligament portions to detect the expression of cell differentiation markers (e.g., alpha-smooth muscle actin and desmin) or markers of tendon or ligament proliferation and/or differentiation (Type I collagen, Type III collagen, tenascin C, and scleraxis).

In some cases, tendon and ligament tissue composites can be coated with formulations to ensure or reduce adherence of the composite to target tissues. For example, tendon or ligament tissue composites can be coated with lubricating agents such as hyaluronic acid or lubricin to reduce adhesion on gliding surfaces. In some cases, tendon or ligament tissue composites can be coated with autologous periosteum or synovium to facilitate adherence to attachment sites (e.g., tendon or bone). In some cases, tendon and ligament tissue composites can be reinforced by adding one or more layers of man-made material, such as silk fabric, to increase the strength and stiffness of the composites. In some cases, tendon and ligament tissue composites can be impregnated with growth factors to stimulate differentiation of the seeded cells. For example, tendon and ligament tissue composites can be impregnated with growth factors or neuropeptides such as transforming growth factor beta (TGF-β), growth differentiation factor-5 (GDF-5), or substance P. Other growth factors appropriate for the methods and materials provided herein can include, for example: platelet derived growth factor (PDGF), basic fibroblast growth factor (b-FGF), insulin like growth factor (IGF), epidermal growth factor (EGF), bone morphogenetic protein (BMP), and vascular endothelial growth factor (VEGF).

This document also provides methods and materials for repairing and replacing damaged tendon and ligament tissue. As described herein, tendon or ligament composites can be surgically implanted in a mammal to replace or repair damaged tissue. For example, a tendon tissue composite seeded with autologous stem cells can be implanted into a mammal at the site of tendon tissue damage. In some cases, a ligament tissue composite seeded with autologous stem cells can be implanted into a mammal ay the site of ligament tissue damage. Tendons that can be repaired or replaced by the methods described herein can include, for example, the Achilles tendon, infraspinatus tendon, tibialis anterior tendon, peroneus longus tendon, peroneus medius tendon, extensor digitorum longus tendons, extensor hallucis longus tendon, flexor digitorum longus tendon, or patellar tendon. Ligaments that can be repaired or replaced by the methods described herein can include, for example, the ulnar collateral ligament, radial collateral ligament, medical collateral ligament, lateral collateral ligament, anterior cruciate ligament, posterior cruciate ligament, anterior or posterior talofibular ligaments, calcaneofibular ligament, talocalcaneal ligament, or posterior talocalcaneal ligament.

In some cases, a tendon or ligament composite can be surgically implanted into a mammal. For example, a tendon or ligament composite can be surgically implanted to reconstruct, for example, a defect in a knee ligament or shoulder rotator cuff tendon. In some cases, a tendon or ligament composite can be surgically implanted to replace a damaged finger tendon or to lengthen a tendon graft.

Any appropriate method(s) can be performed to assay for tendon or ligament tissue repair or for the replacement of damaged tendon or ligament tissue. For example, methods can be performed to assess tissue healing, to assess functionality of repaired or replaced tendons or ligaments, and to assess cellular ingrowth. As described previously, histology and cell staining can be performed to detect seeded cell propagation. In some cases, physiological tests, including ultrasound assessment of tendon integrity and motion, can be performed to assess movement and functionality of tendons or ligaments following surgical implantation of tendon or ligament composites.

The invention will be further described in the following examples, which do not limit the scope of the invention described in the claims.

EXAMPLES

Example 1

Bone Marrow Stromal Cells Harvest

Twenty mixed-breed dogs weighing between 25 and 30 kg were used for bone marrow and tendon tissue harvesting. Immediately prior to sacrifice, the dogs were anesthetized with intravenous ketamine (13 mg/kg) and diazepam (6 mg/kg) and maintained under anesthesia with 1.5% isoflurane. A total of 4.0 mL of bone marrow was aspirated from the medial aspect of the proximal tibiae using an 18G needle and 20 mL syringe (BD, Franklin Lakes, N.J.) containing 1.0 mL of heparin solution (Heparin sodium injection, Baxter Healthcare Corporation, Deerfield, Ill.). The dogs were then euthanized by an overdose of pentobarbital, and the infraspinatus tendons of both shoulders were harvested. The infraspinatus tendon was exposed by removing the deltoid muscle, and the tendinous portion between the insertion to the bone and the muscle-tendon junction was harvested. The size of harvested tendon was roughly 25×10 mm, and rectangular in shape. The harvested tendons were frozen at −80° C. until processing. Both the bone marrow and infraspinatus tendons were harvested under sterile conditions. The donor of the BMSC was not matched with the donor of the tendon in making the composite of BMSC and tendon slices for this in vitro experiment.

The heparinized bone marrow extract was added to 5.0 mL phosphate buffered saline (PBS), and centrifuged at 1500 rpm (380 g) for 5 minutes at room temperature. The bone marrow pellet was resolubilized in 10 mL of minimal essential medium (MEM) with Earle's salts (GIBCO, Grand Island, N.Y.), 10% fetal bovine serum (GIBCO), and 5% antibiotics (Antibiotic-Antimycotic, GIBCO). The cells from one dog were divided into four equal aliquots, placed in 100-mm culture dishes and incubated at 37° C. with 5% $CO_2$ and 95% air at 100% humidity. After 5 days, the medium and any floating cells were removed and new medium was added to the remaining adherent cells. These adherent cells were defined as bone marrow stromal cells (BMSC). The medium was then changed every other day until the cells reached confluence. The cells were then released with trypsin-EDTA solution (0.25% trypsin, 0.1% EDTA in HBSS, Mediatech Inc., Manassas, Va.) to produce a cell suspension, and centrifuged at 1500 rpm for 5 minutes to remove the trypsin-EDTA solution. The concentrated cell suspension from each dog was then gathered in one tube. The cells were counted with a hemacytometer, and the concentration of the cell suspension was adjusted to $5.0 \times 10^6$ cells/mL by adding additional medium.

Example 2

Multilayer Sliced Acellular Tendon Scaffold

Frozen infraspinatus tendon was thawed at room temperature. The infraspinatus tendons were trimmed into segments roughly 25×10 mm in size. The tendon segments were immersed in liquid nitrogen for 2 minutes and then thawed in saline solution at 37° C. for 10 minutes. This procedure was repeated five times. Following washing in phosphate buffered saline (PBS) without EDTA (3×30 minutes), the tendon segments were incubated in 20 mL of nuclease solution from bovine pancreas, 1.5 Units/mL, Roche Diagnostic, Indianapolis, Ind.) for 12 hours at 37° C. Finally, the infraspinatus tendon segments were rinsed for 30 minutes in PBS (50 mL) at room temperature with gentle agitation. The rinsing was repeated three times. The tendon segments were then frozen to −80° C. and fixed to the cutting base plate of a cryostat (Leica CM1850, Germany) with O.C.T. compound (polyvinyl alcohol and polyethylene glycol, Tissue-Tek., Sakura Finetek USA, Inc., Torrance, Calif.). The excess O.C.T. compound around the tendon was removed by a scalpel. The tendon segments were then sliced at a thickness of 50 μm and the slices were placed in a 100-mm culture dish. Ten slices were placed on each dish. The slices were thawed on the dish in an incubator at 37° C. with 5% $CO_2$ and 95% air at 100% humidity for 10 minutes. The tendon slices were then washed three times with 10 mL of PBS. At this point, the sliced acellular tendon segments were ready to seed with BMSC.

Example 3

Composite of BMSC and Sliced Tendon Scaffold

The concentrated bone marrow stromal cell (BMSC) solution ($5.0 \times 10^6$ cells/mL, 10 mL/dish) was added to the sliced tendon scaffold dish and cultured at 37° C. with 5% $CO_2$ and 95% air at 100% humidity for 2 days. The slices were then carefully detached with forceps and bundled together on a new dish. The ends of the bundled slices were fixed with 3-0 Ethilon suture (nylon suture, Ethicon Inc., Piscataway, N.J.), and a 1.2 g sterilized stainless steel clip (Alligator clip, Mueller Electric Company, Cleveland, Ohio) was attached at one end of the sutured bundle. The composite was then suspended in a 15 mL conical tube and immersed in the same medium described above. The clip served as a weight, preventing the composite from floating in the medium. The composites were incubated for 2, 7, or 14 days. As a control, tendon slices without cells were bundled and maintained in medium for the same time periods. The medium was changed every other day.

Example 4

Assessment of Cell Viability

BMSC from 2 dogs were stained with the fluorescent marker PKH26-GL (PKH26 Red Fluorescent Cell Linker Kit for General Cell Membrane Labeling, Sigma, Saint Louis, Mo.) before seeding on the tendon slices, following the manufacturer's instructions. This fluorescent marker has been used for cell tracking in the studies using bone marrow stromal cells. Prior to bundling (i.e., after 2 days in culture), single tendon slices with labeled BMSC were examined by a laser scanning confocal microscope (LSM310, Zeiss) without fixation. For the evaluation of the composites incubated for 7 and 14 days, frozen sections of the composite were made at a thickness of 50 μm, and then examined under the confocal microscope. The fluorescent image of the composite after incubation was combined with the image under the ultraviolet light, with the tendon slices observed as blue under the ultraviolet light.

Example 5

Histological Assessment

The 7 and 14 day incubation composites from 2 dogs were used for the histological assessment. The tendon slices without BMSC incubated in the medium for 2 days were also used to evaluate whether any host cells remained after repeated freeze-thaw cycles. These samples were fixed in 10% neutral buffered formalin, embedded in paraffin, and sectioned longitudinally at a thickness of 5 μm. Hematoxylin and eosin staining was performed.

Figure 2:
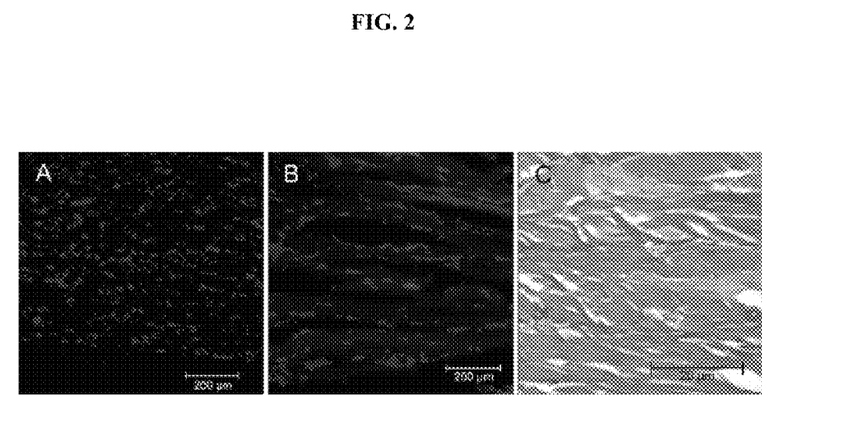
FIG. 2 contains photographs of tendon slices. (A) BMSC were observed on one tendon slice detached from dish before bundling, after 2 days incubation. (B) Labeled BMSC were observed on and between tendon slices after 14 days incubation. The image combines a fluorescent red label and a non-specific blue ultraviolet background. (C) Hematoxylin and eosin stained section showed dense collagen fibers of the tendon slices, and cells located between tendon slices after a 14 day incubation (original magnification ×200).

Histology showed that the seeded cells aligned between the collagen fibers of the tendon slices. The BMSC labeled with PKH26 were observed as red under the confocal laser microscope (FIG. 2A, Red: BMSC). After 2 days in culture, viable BMSCs were observed on single slices before bundling. In the bundled composites, the BMSCs were also observed between slices after 7 and 14 days in culture (FIG. 2B, longitudinal image, 14 days of incubation). Cells were not observed in the unseeded tendon slices after five freeze-thaw cycles. In the composite of BMSC and tendon slices after 7 and 14 days of incubation, histological sections showed most cells existed between the tendon slices (FIG. 2C, original magnification ×200, 14 days of incubation).

Example 6

Assessment of Gene Expression

A quantitative real-time reverse transcription-polymerase chain reaction (RT-PCR) was performed to measure the gene expression levels of tenomodulin (a marker of tenocyte differentiation), collagen type I and III, MMP2 (gelatinase), and MMP13 (collagenase). RNA was extracted by TRIZOL® reagent (monophasic solutions of phenol and guanidine isothiocyanate, Invitrogen Corporation, Carlsbad, Calif.). cDNA was synthesized using 1st Strand cDNA Synthesis Kit (Roche) with random primers. The sequences of the primers are shown in Table 1. The expression level was normalized to that of GAPDH. All mRNA expressions were confirmed by melting curve analysis using LIGHTCYCLER® system (Roche). Eight samples from each group, including the BMSC solution before seeding, the composites incubated for 2, 7, and 14 days, and the intact infraspinatus tendons were used for assessment of gene expression.

TABLE 1

Forward and Reverse Primer Sequences

| Gene | Sequences of forward and reverse primers |
|---|---|
| GAPDH | F: 5'-TATGATTCTACCCACGGCAA-3' (SEQ ID NO: 1)<br>R: 5'-CAGTGGACTCCACAACATAC-3' (SEQ ID NO: 2) |
| Collagen Type I | F: 5'-TGGTTCTCCTGGCAAAGAT-3' (SEQ ID NO: 3)<br>R: 5'-ATCACCGGGTTCACCTTTA-3' (SEQ ID NO: 4) |
| Collagen Type III | F: 5'-ACAGCAGCAAGCTATTGAT-3' (SEQ ID NO: 5)<br>R: 5'-GGACAGTCTAATTCTTGTTCGT-3' (SEQ ID NO: 6) |
| MMP2 | F: 5'-AGCTACTTCTTCAAGGGTG-3' (SEQ ID NO: 7)<br>R: 5'-GTGTGCAGAAGGACCTG-3' (SEQ ID NO: 8) |
| MMP13 | F: 5'-TACAACTTGTTCCTTGTCGC-3' (SEQ ID NO: 9)<br>R: 5'-CTGGGCCATAGAGAGACT-3' (SEQ ID NO: 10) |
| Tenomodulin | F: 5'-GATCCCATGCTGGATGAG-3' (SEQ ID NO: 11)<br>R: 5'-TACAAGGCATGATGACAGC-3' (SEQ ID NO: 12) |

Figure 3:
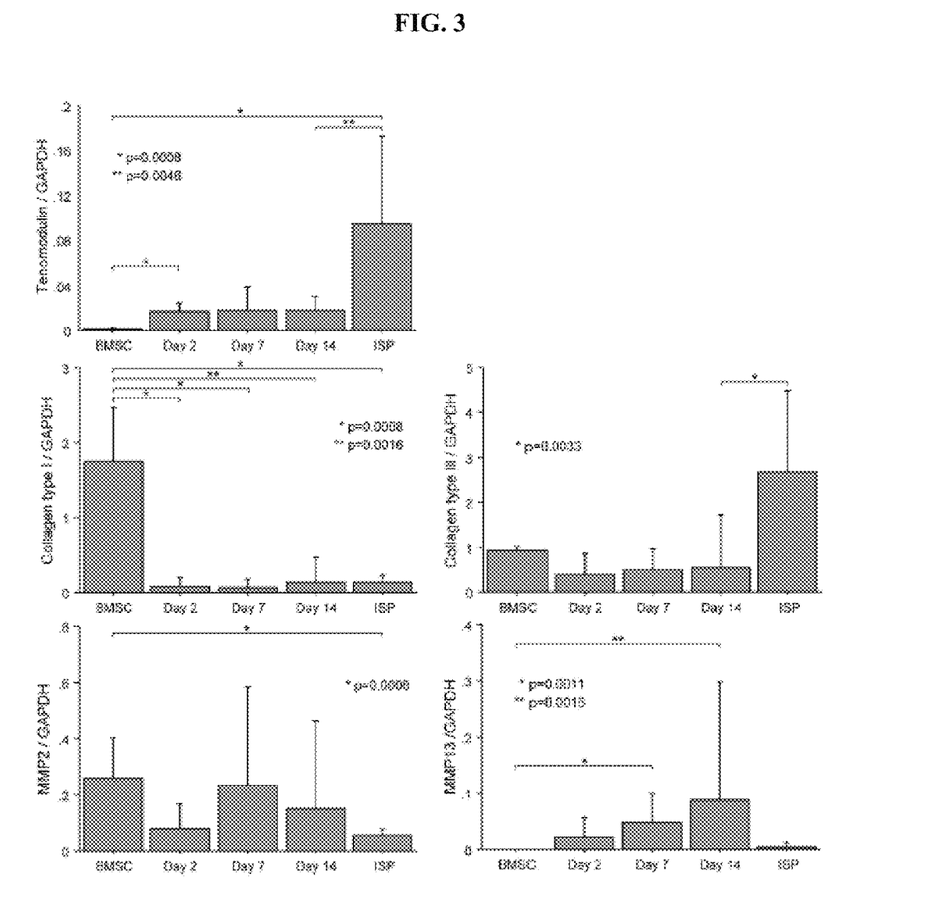
FIG. 3 contains the results of gene expression analysis of tenomodulin, collagen type I, collagen type III, MMP2, and MMP13 by qRT-PCR. Expression levels were normalized to that of GAPDH (n=8).

Gene expression data are shown in FIG. 3. In the decellularized tendon slices without BMSC, GAPDH and other gene expression were not detected. In contrast, the native ISP tendon showed high expression of tenomodulin and type III collagen, with low expression of type I collagen and MMPs. BMSC before seeding showed no detectable tenomodulin or MMP13 but did show high (2×GAPDH) expression of type I collagen and MMP2, and moderate (1×GAPDH) expression of type III collagen. In general, the composites showed high levels of tenomodulin expression and low levels of expression of collagen I and III compared to the BMSC before seeding, which suggests that seeded BMSC in the tendon composite can differentiate into tendon-like cells. By day 7, the expression of MMPs had increased, significantly so for MMP13, as compared to the cultured BMSC alone. 14-day composites showed a similar trend.

Figure 4:
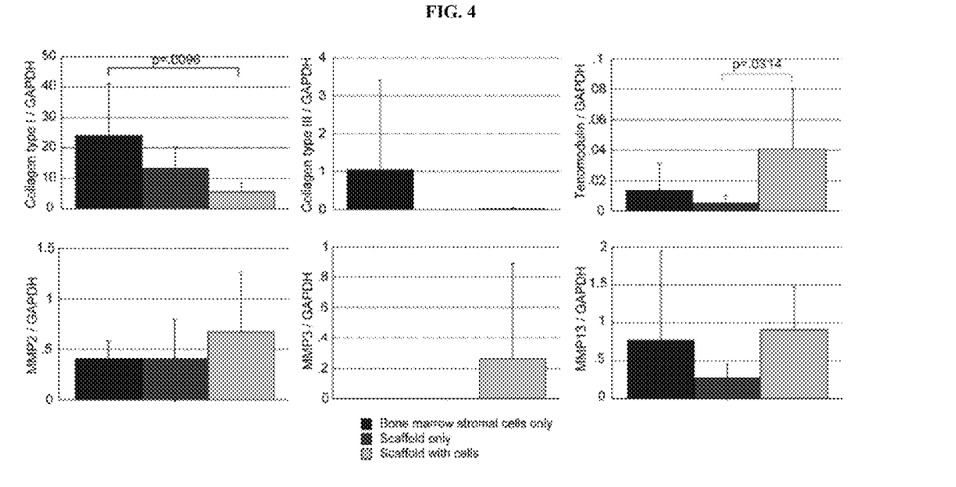
FIG. 4 contains the results of gene expression analysis of tenomodulin, collagen type I, collagen type III, MMP2, MMP3, and MMP13 in bone marrow stromal cells only, scaffold only, and scaffold seeded with BMSCs. Expression levels were normalized to that of GAPDH (n=6).
Figure 7:
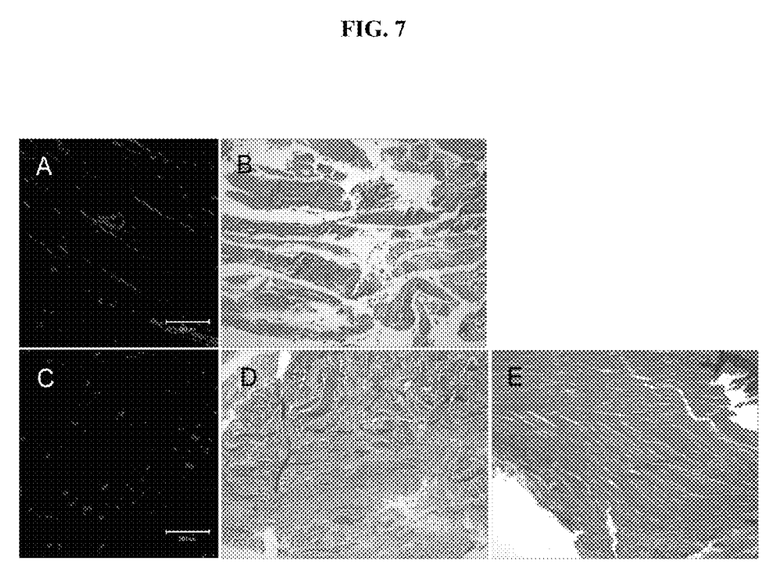
FIG. 7 contains photographs of tendon slices. (A and B) tendon tissue composite seeded with BMSC pre-transplantation. (C and D) tissue composite seeded with BMSC 14 days post-transplantation. (E) tendon slices without BMSC 14 days post-transplantation. Tissue in B, D, and E stained with hematoxylin and eosin (original magnification ×100).

In vivo assays were performed using a rabbit model. Two weeks following transplantation of a BMSC-seeded tendon tissue composite to replace the middle potion of the patellar tendon, it was evident that BMSCs had successfully survived (FIG. 7). Gene expression assays detected high levels of expression of tenomodulin and the MMPs in tissue composites with seeded BMSC as compared to the tissue composite scaffold alone. These data suggest that BMSC might express a tendon phenotype in vivo. Furthermore, changes of collagen and MMP expression suggest that the BMSC also have an effect on collagen metabolism. This new composite might be useful as a model of tendon tissue engineering (FIG. 4).

Example 7

Biomechanical Assessment

Figure 1:
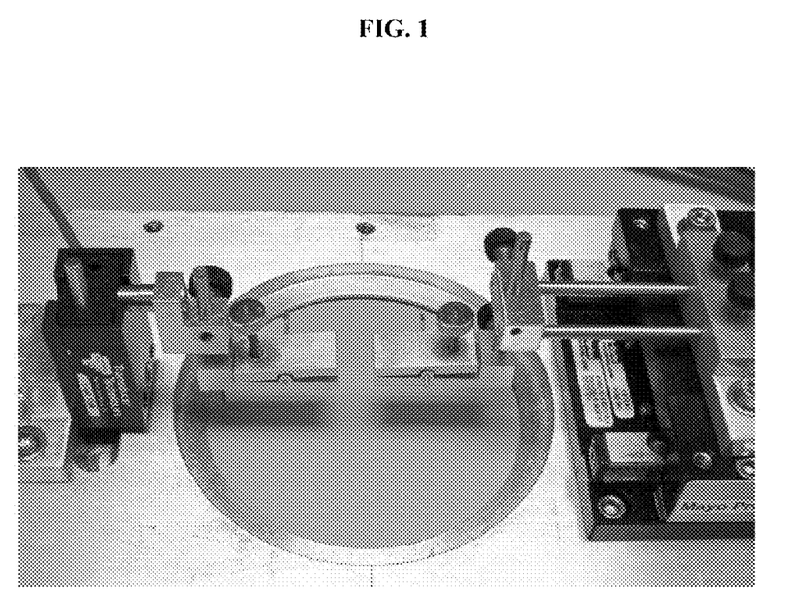
FIG. 1 is a photograph of a microtester used for testing the mechanical properties of tendon slices.

The maximum failure load and the linear stiffness of the composite were measured with a custom-made microtester, which was composed of a linear servo motor (MX 80 Daedal, Irwin, Pa., USA) and a load cell with the accuracy of 0.01N (MDB-5, Transducer Techniques, Temecula, Calif., USA). The composites with BMSC from 8 dogs after 7 and 14 days incubation were used. Both sides of the tendon, at a length of 10 mm, were clamped with a custom designed holder and 0.1N of preload was applied (FIG. 1). The composite was distracted at a rate of 0.2 mm/second. This assessment was performed immediately after the end of each culture, and the composites were kept moist with PBS during measurement. The ultimate tensile load and the stiffness of the tendon slice were recorded and analyzed. The ultimate tensile load was defined as the maximum load to break the tendon slice. The stiffness was defined as the slope of the load/displacement curve in the linear region.

The results of the maximum failure load and the linear stiffness were analyzed by two-way ANOVA, and the results of the gene expressions were analyzed by the Kruskal-Wallis test and Mann-Whitney test, with Bonferroni post hoc adjustment. The non-parametric analysis was used because the gene expression results had large standard deviations, which are not suitable for parametric analysis. All results with $p<0.05$ were considered significant.

Figure 5:
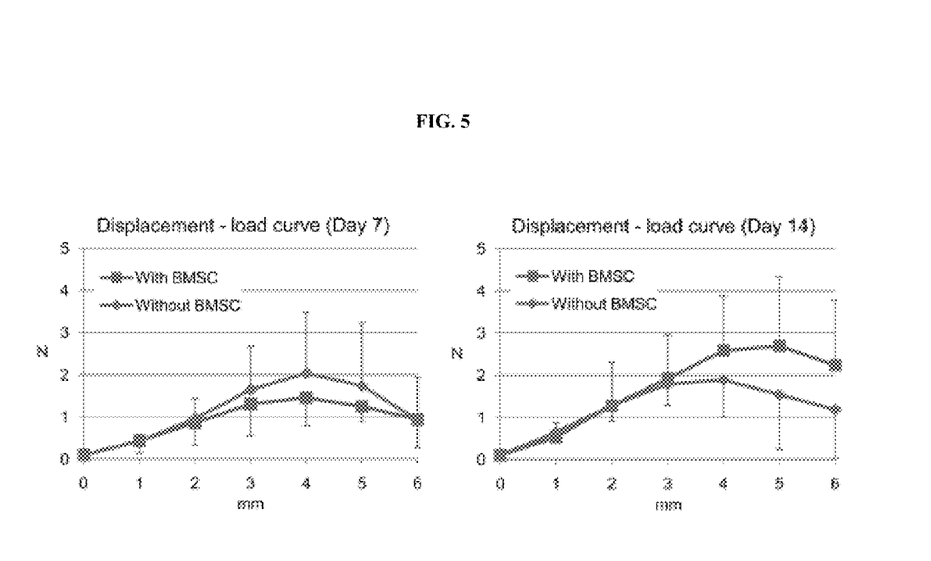
FIG. 5 is a graph of a displacement-load curve after 7 and 14 days of incubation (n=8).
Figure 6:
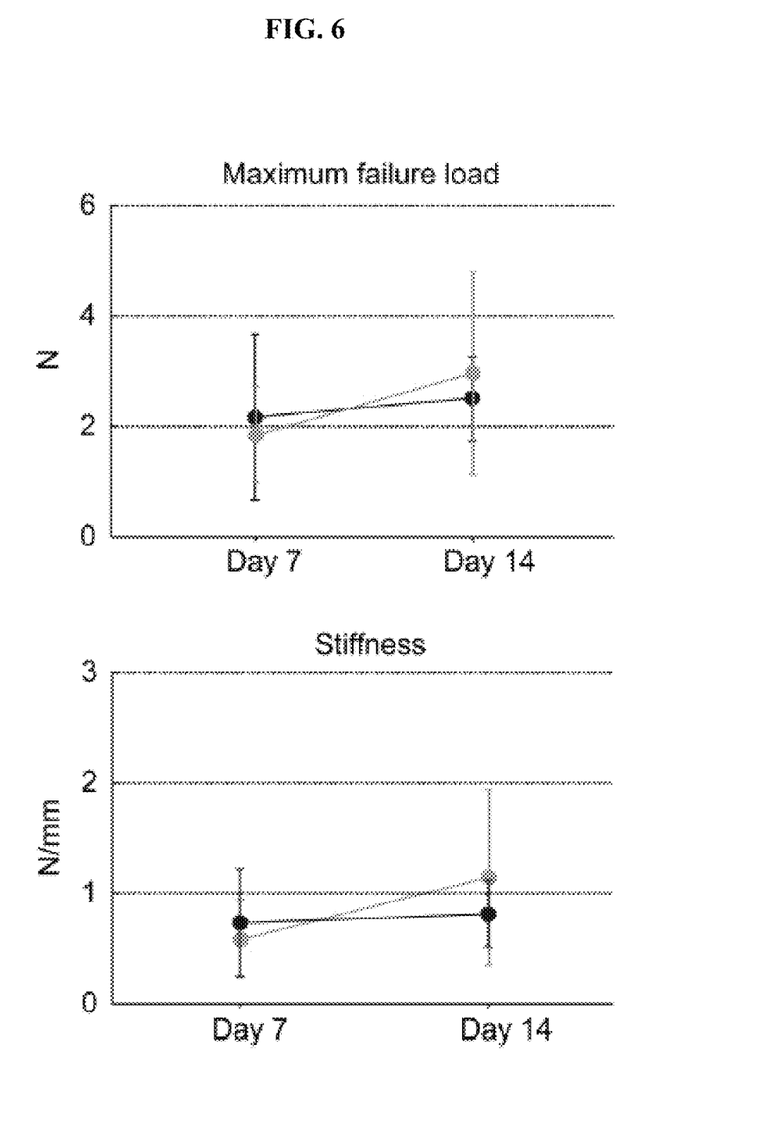
FIG. 6 contains the results of a pull-out test of maximum failure load and stiffness after 7 and 14 days incubation (n=8). Black bars=scaffold only; gray bars=scaffold seeded with BMSCs.

As demonstrated in FIGS. 5 and 6, mechanical testing revealed no significant differences between scaffolds with or without BMSC. The maximum failure load of the composite with BMSC was 1.85±0.86N and 2.97±1.83N at day 7 and 14, respectively. The maximum failure load of the composite without BMSC was 2.13±1.50N and 2.45±0.76N at day 7 and 14, respectively. The linear stiffness of the composite with BMSC was 0.59±0.35N/mm and 1.14±0.80N/mm at day 7 and 14, respectively. The linear stiffness of the composite without BMSC was 0.74±0.48N/mm and 0.82±0.30N/mm at day 7 and 14 respectively. There was no significant difference between scaffolds with or without BMSC, or by time in culture. These results suggest that BMSC do not significantly alter the mechanical properties of the scaffolds within a two-week period. It is possible that two weeks in cell culture may be insufficient for substantial remodeling of the tendon substrate by the implanted cells, and so the mechanical properties are, not surprisingly, similar in all groups.

Example 8

Mechanical Characteristics of Native Tendon Slices for Engineered Tendon Scaffolds Engineered tendon scaffolds require appropriate mechanical strength, pore size and porosity for temporary mechanical support, cell infiltration and survival. Tendon extracellular matrix (ECM) components play important roles in modulating the biological activities of tendon fibroblasts or tendon stem cells. In order to develop a scaffold to possess the sufficient mechanical strength, efficient cell seeding area, and natural ECM micro-architecture of native tendons, it was proposed that the scaffold be made from acellular tendon slices.

Figure 8:
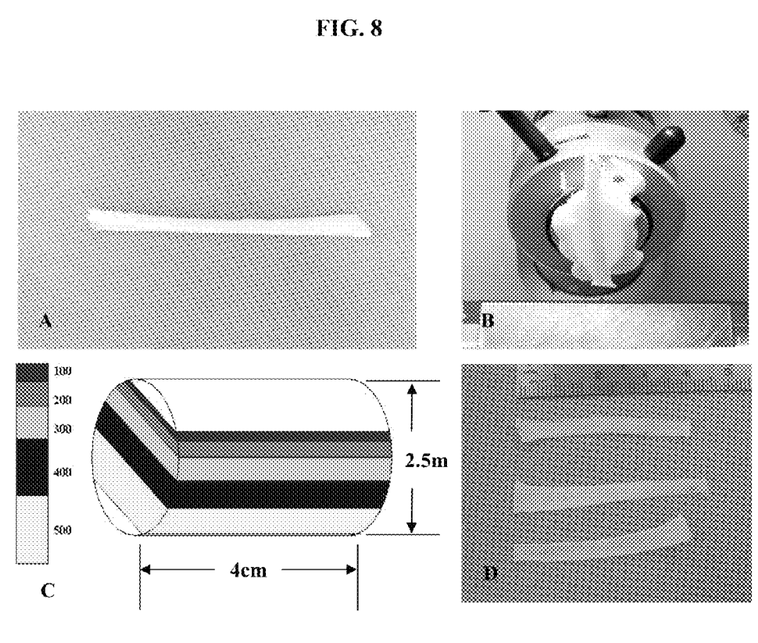
FIG. 8 contains photographs and a schematic representation of Achilles tendon (AT) bundles. (A) a single bundle of the AT tendon. (B, C, and D) Each AT tendon bundle was sectioned with a cryostat into 5 different thicknesses of slices at 100, 200, 300, 400, and 500 micrometers (μm) in succession.

The mechanical characteristics of native tendon slices were determined to identify the minimum thickness of tendon slice that maintains the fundamental mechanical characteristics of native tendon. It was hypothesized that there would be mechanical alterations with varying thicknesses of native tendon slices. Eight hind limbs were obtained from four dogs that were euthanized for studies approved by the Institutional Animal Care and Use Committee. Three bundles of each Achilles tendon (AT) were dissected from each hind limb. Each bundle was embedded in Tissue-Tek® optimal cutting temperature compound (Sakura Finetek USA, Inc., USA) and sliced with the thickness of 100, 200, 300, 400, or 500 μm in succession on a cryostat (Leica CM1850, Germany) (FIG. 8). AT bundles (n=10) and AT slices (n=50) were used. The ends of the AT bundles and slices were wrapped with saline-soaked gauze and mounted into custom-made grips on an uniaxial load frame (MTS 312, MTS Co., MA) for failure testing. Cross-sectional area and the distance between the grips were measured prior to testing with a digital caliper. Bundles and slices were pre-loaded to 0.2 N, and then stretched to failure at a rate of 0.2 mm/s. Samples were kept moist during testing with saline. Ultimate tensile stress (UTS), failure strain, and elastic modulus were calculated from the load and displacement data obtained from the test.

Figure 9:
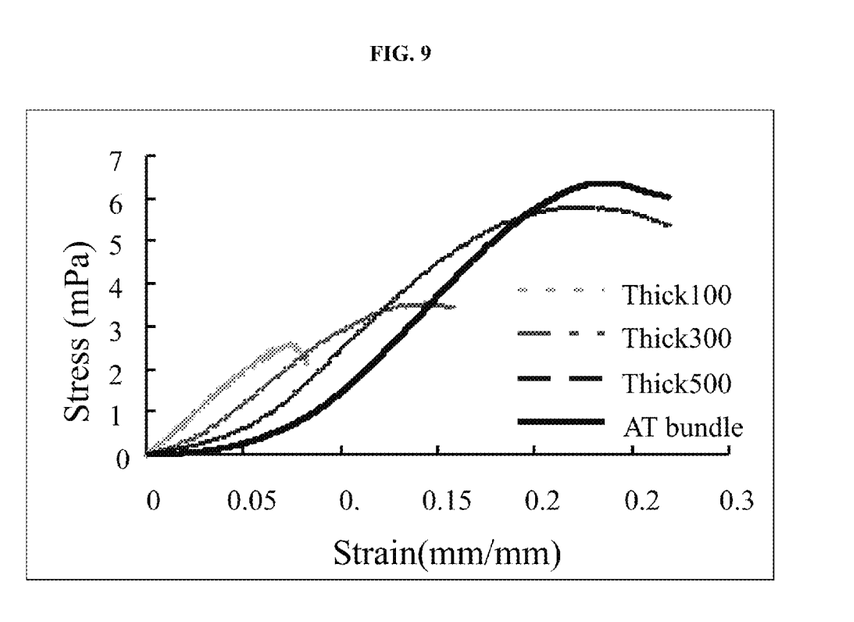
FIG. 9 is a graph depicting typical stress-strain curves of AT slices and bundle.
Figure 10:
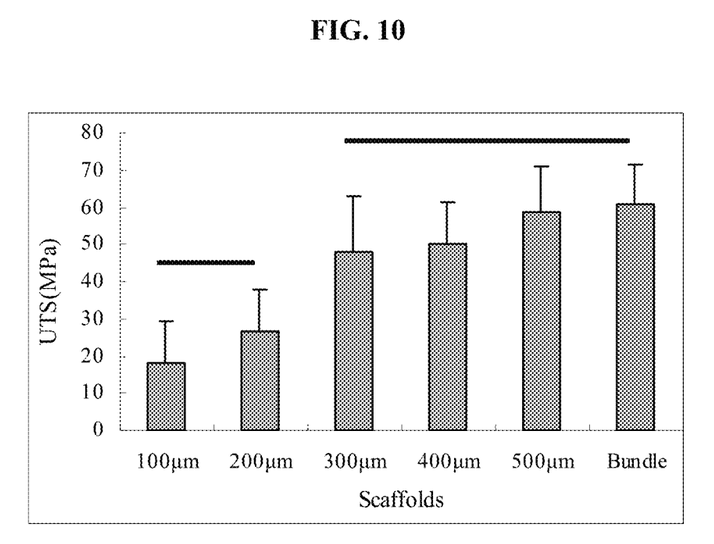
FIG. 10 is a graph depicting the ultimate tensile stress (UTS) of AT slices and bundle. The lines connect values with no significant difference.
Figure 11:
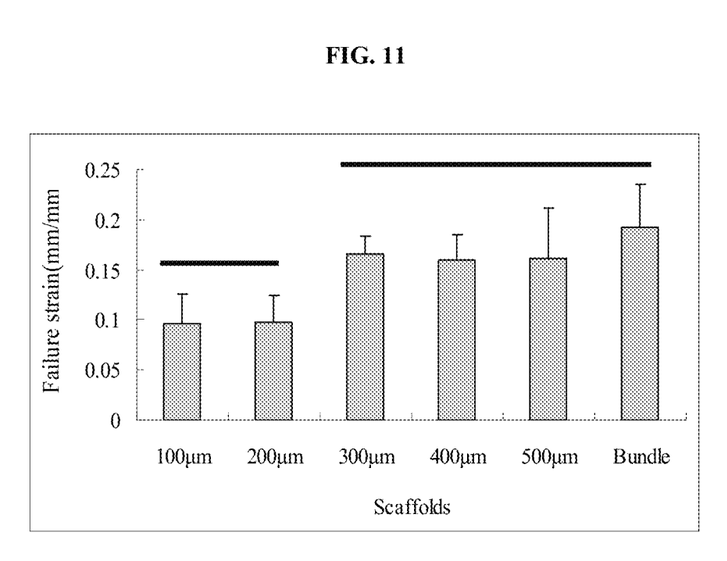
FIG. 11 contains the results of a failure strain assay.

Typical stress-strain curves for the AT bundle and representative slices are shown in FIG. 9. For the slices with thicknesses of more than 300 μm, the toe regions were apparent, followed by linear regions, which continued until ultimate failure. The mean UTS and modulus values exhibited a gradual rise with increasing thickness. The UTS of tendon slices of 300 μm, 400 μm, 500 μm, and tendon bundle was significantly higher than the slices of 100 μm and 200 μm ($p<0.05$). There was no significant difference among 300 μm, 400 μm, 500 μm, and tendon bundle (FIG. 10). For 300 μm thick slices, the UTS and modulus reached mean values of approximately 78 and 81 percent of AT bundles, respectively. The failure strain of 300 μm thick slice was remarkably higher than that of 100 or 200 μm thick slice, reaching a mean value of 87 percent of native AT bundles. There was no significant difference in failure strain among 300 μm, 400 μm, 500 μm AT slices and tendon bundle (FIG. 11).

The tendon is a fibrous connective tissue, consisting predominantly of type I collagen fibers. The collagen fibrils follow a natural periodic crimp, which is planar with respect to the alignment of the tendon structure. According to hierarchical arrangement of the tendon, the dimension of fibers with crimp waveform is approximately 20 μm, and the dimension of mature fascicles is roughly 200 μm. Slice thickness less than 200 μm would be likely to damage the crimp structure and fascicles, and result in structural weakening. In contrast, the slices with thickness of 300 μm or more should preserve most of the crimp structure and collagen fibril integrity. These data confirmed this hypothesis, as the slices with thickness of 300 μm or more exhibited a standard stress-strain curve similar to the native AT bundles.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising multiple layers of decellularized tendon or ligament portions, wherein said portions were obtained from a mammal, wherein each layer of said multiple layers is between 200 µm and 500 µm thick, and wherein said composition is further seeded with a plurality of cells.

2. The composition of claim 1, wherein said composition comprises tendon portions.

3. The composition of claim 1, wherein said composition comprises ligament portions.

4. The composition of claim 1, wherein each layer of said multiple layers is about 300 µm thick.

5. The composition of claim 1, further comprising an extracellular matrix of said tendon or ligament portions.

6. The composition of claim 1, wherein said mammal is a human.

7. The composition of claim 1, wherein said plurality of cells are stem cells autologous to said mammal.

8. The composition of claim 7, wherein said stem cells are derived from bone marrow, tendon, ligament, muscle, adipose, or synovial tissue of said mammal.

9. The composition of claim 1, wherein said composition is coated with a lubricating surface.

10. The composition of claim 1, further comprising one or more growth factors.

11. The composition of claim 10, wherein said growth factors are GDF5, TGF-β, VEGF, PDGF, BMPs, or any combination thereof.

12. The composition of claim 1, wherein said composition is reinforced by adding one or more layers of man-made material.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 1
tatgattcta cccacggcaa                                          20

<210> SEQ ID NO 2
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 2
cagtggactc cacaacatac                                          20

```
<210> SEQ ID NO 3
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 3
tggttctcct ggcaaagat                                                  19

<210> SEQ ID NO 4
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 4
atcaccgggt tcaccttta                                                  19

<210> SEQ ID NO 5
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 5
acagcagcaa gctattgat                                                  19

<210> SEQ ID NO 6
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 6
ggacagtcta attcttgttc gt                                              22

<210> SEQ ID NO 7
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 7
agctacttct tcaagggtg                                                  19

<210> SEQ ID NO 8
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 8
gtgtgcagaa ggacctg                                                    17

<210> SEQ ID NO 9
<211> LENGTH: 20
<212> TYPE: DNA
<213> ORGANISM: Artificial Sequence
<220> FEATURE:
<223> OTHER INFORMATION: synthetic oligonucleotide
```

```
<400> SEQUENCE: 9
tacaacttgt tccttgtcgc                                              20

<210> SEQ ID NO 10
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 10
ctgggccata gagagact                                                18

<210> SEQ ID NO 11
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 11
gatcccatgc tggatgag                                                18

<210> SEQ ID NO 12
<211> LENGTH: 19
<212> TYPE: DNA
<213> ORGANISM: Artificial Sequence
<220> FEATURE:
<223> OTHER INFORMATION: synthetic oligonucleotide

<400> SEQUENCE: 12
tacaaggcat gatgacagc                                               19
```